United States Patent [19]

Dudar et al.

[11] Patent Number: 4,850,978
[45] Date of Patent: Jul. 25, 1989

[54] DRUG DELIVERY CARTRIDGE WITH PROTECTIVE COVER

[75] Inventors: Thomas E. Dudar, Palatine; Brian D. Zdeb, Round Lake Park, both of Ill.

[73] Assignee: Baxter International Inc., Deerfield, Ill.

[21] Appl. No.: 114,814

[22] Filed: Oct. 29, 1987

[51] Int. Cl.⁴ .............................................. A61M 5/24
[52] U.S. Cl. ..................................... 604/201; 604/85; 604/88; 604/263
[58] Field of Search ............................. 604/56, 82–88, 604/91, 92, 411–414, 201, 205, 206, 220, 263

[56] References Cited

U.S. PATENT DOCUMENTS

| | | | |
|---|---|---|---|
| 2,453,590 | 11/1948 | Poux | 604/263 |
| 2,666,434 | 1/1954 | Ogle | 604/88 |
| 2,668,534 | 2/1954 | Barradas et al. | 604/205 X |
| 3,376,866 | 4/1968 | Ogle | 604/206 X |
| 3,490,437 | 1/1970 | Bakondy et al. | 604/88 X |
| 3,584,626 | 6/1971 | Johansson | 604/201 |
| 3,667,652 | 6/1972 | Morane et al. | 604/56 X |
| 3,677,245 | 7/1972 | Welch | 604/201 |
| 3,783,997 | 1/1974 | Brown | 604/201 |
| 3,820,652 | 6/1974 | Thackston | 604/201 X |
| 3,890,971 | 6/1975 | Leeson et al. | 604/220 |
| 3,930,499 | 1/1976 | Rimbaud | 604/201 X |
| 4,328,802 | 5/1982 | Curley et al. | 604/88 |
| 4,445,895 | 5/1984 | Margulies | 604/201 X |
| 4,465,471 | 8/1984 | Harris et al. | 604/92 X |
| 4,534,758 | 8/1985 | Akers et al. | 604/84 X |

Primary Examiner—Ira S. Lazarus
Assistant Examiner—Richard R. Cole
Attorney, Agent, or Firm—Paul E. Schaafsma; Bradford R. L. Price; Paul Flattery

[57] ABSTRACT

A cartridge 444, 644, 744 is adapted for mounting upon a receptacle 442, 642 in a parenterial fluid administration set 420 for delivering a drug or other beneficial agent to a patient. The cartridge 444, 644, 744 includes a beneficial agent-containing chamber 606 slidable from a first, pre-use position to a second, post-use position. The cartridge includes a hollow tube 496 in which the chamber 606 is at least partially mounted. At least one cannula 500 is mounted to the hollow tube and extends opposite the chamber. A protective cover or cap 530 maintains a chamber protective position that prevents inadvertent movement of the chamber that would accidentally engage the cartridge chamber with a flow path member, such as the cannula. The cover is removed in order to engage the chamber. After delivery of the agent to the patient, the cartridge is removed from the receptacle 442,642 and the cover 530 is selectively moved to a cannula protective position in which the cover 530 is securely mounted about the second, opposite end of the hollow tube, covering the cannula 500.

3 Claims, 7 Drawing Sheets

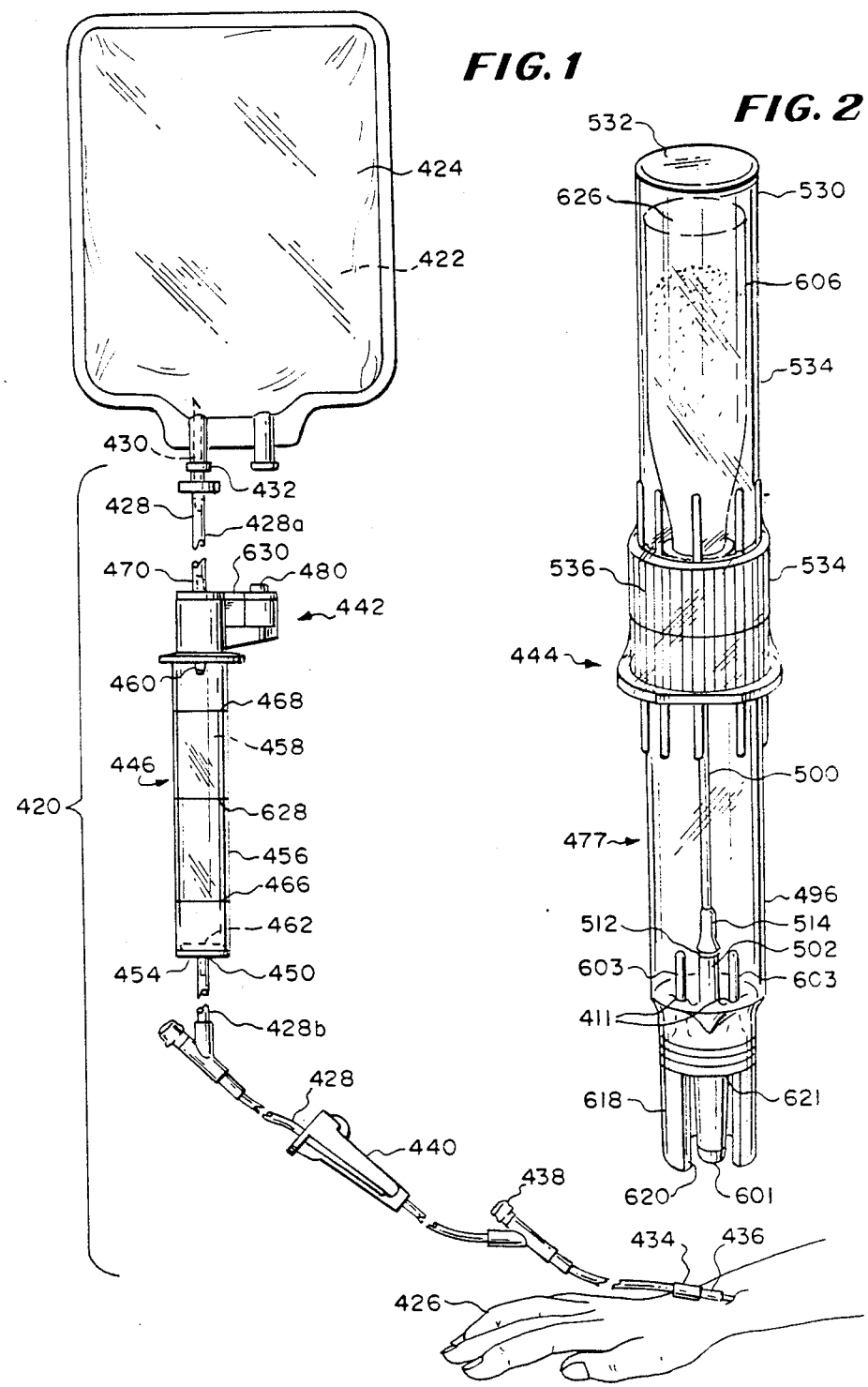

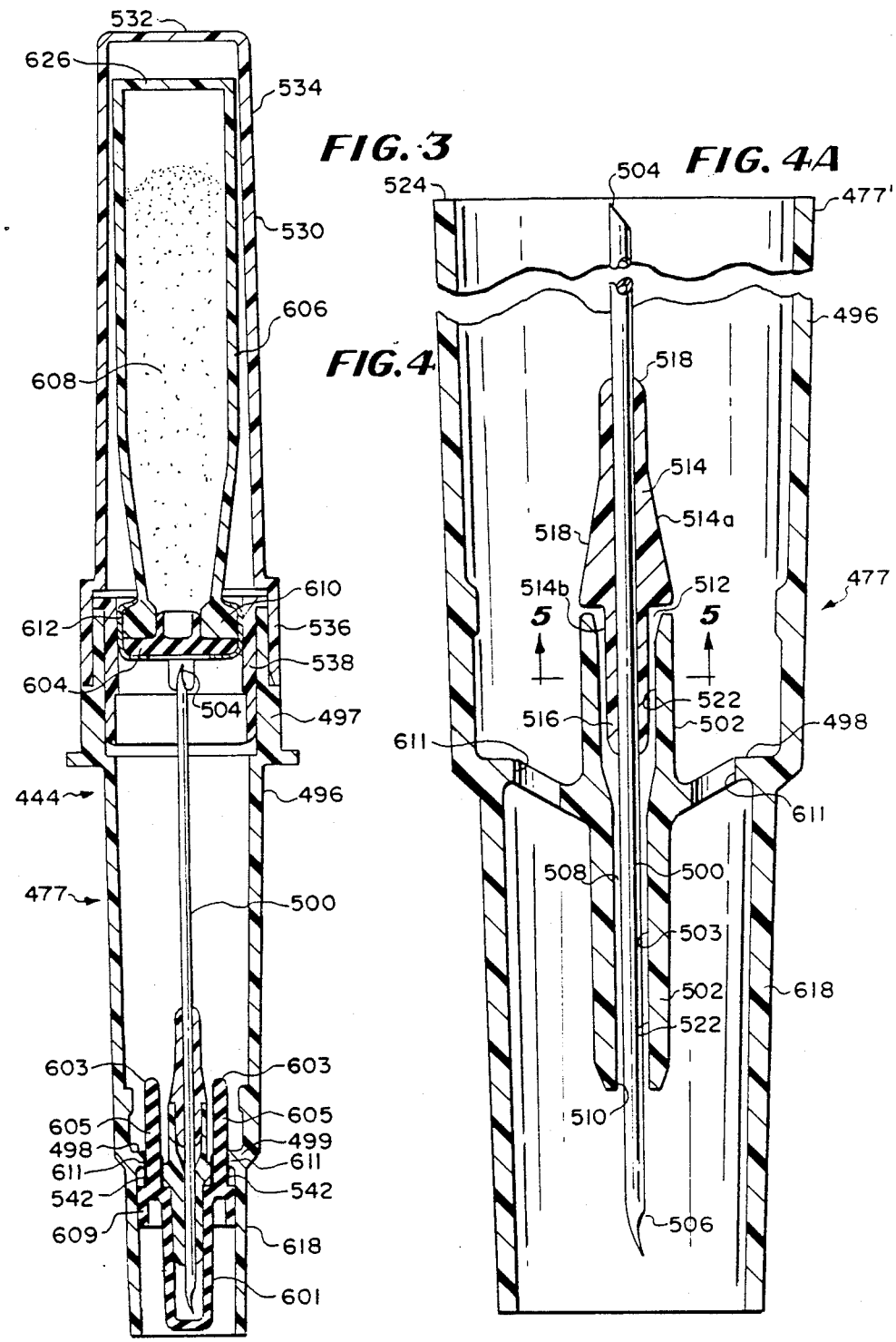

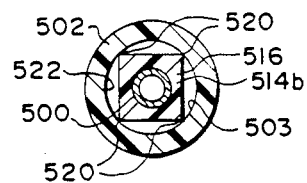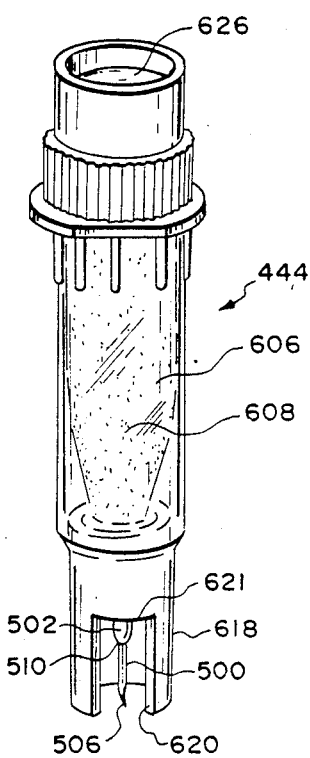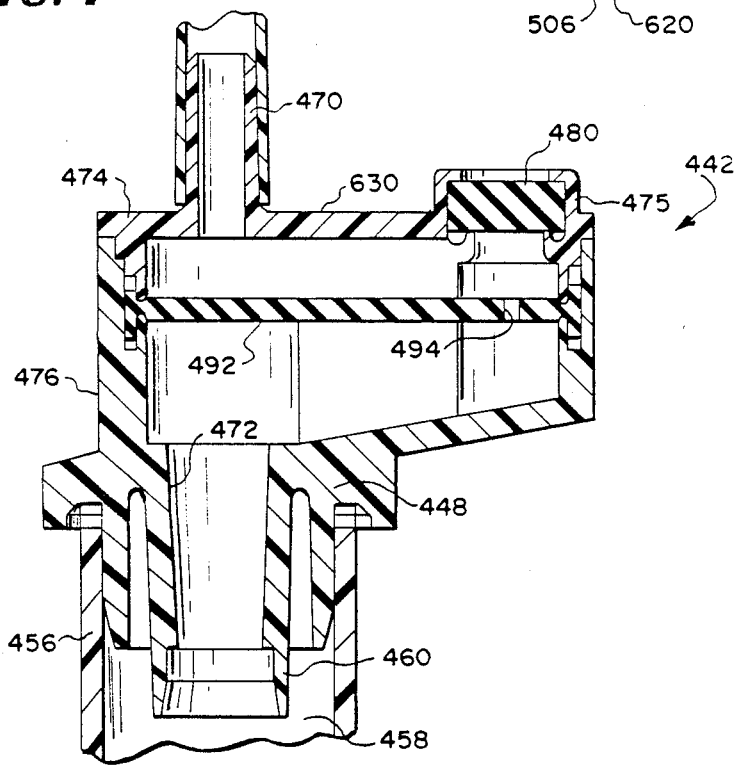

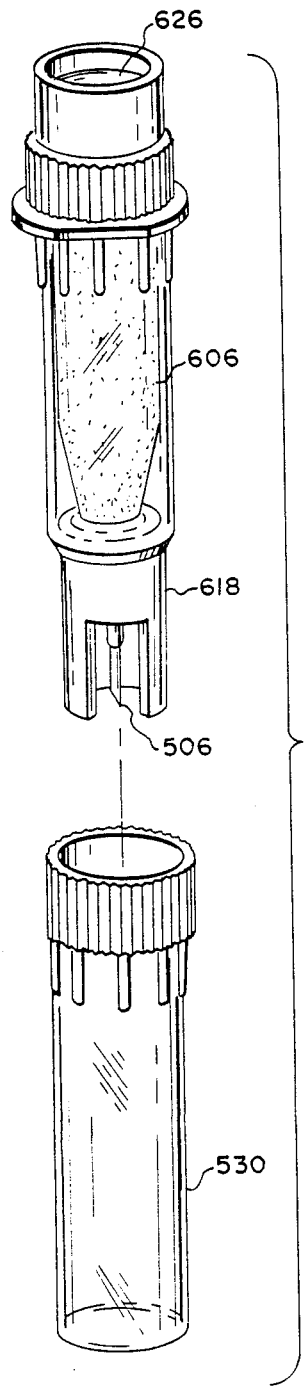
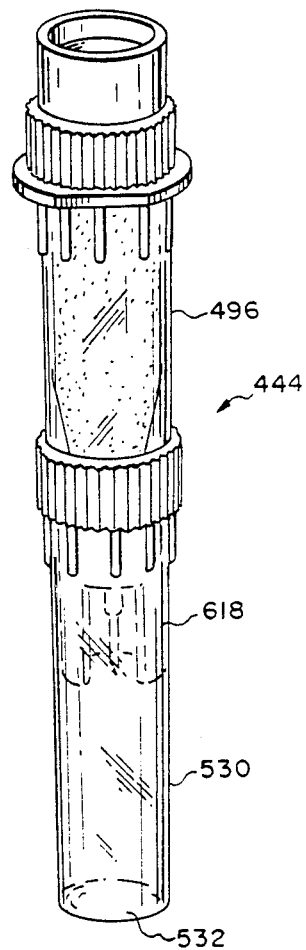
FIG. 10
FIG. 9
444

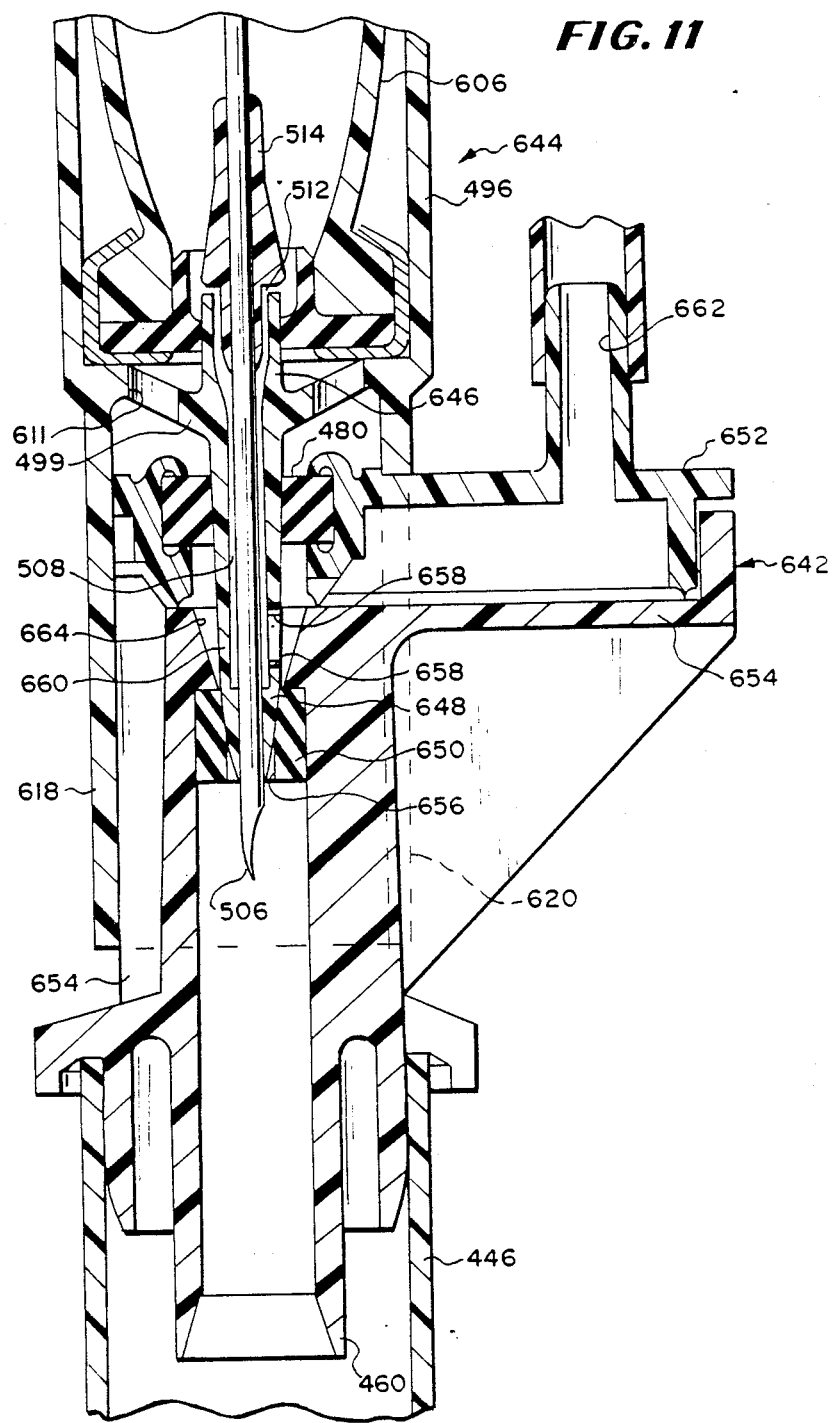

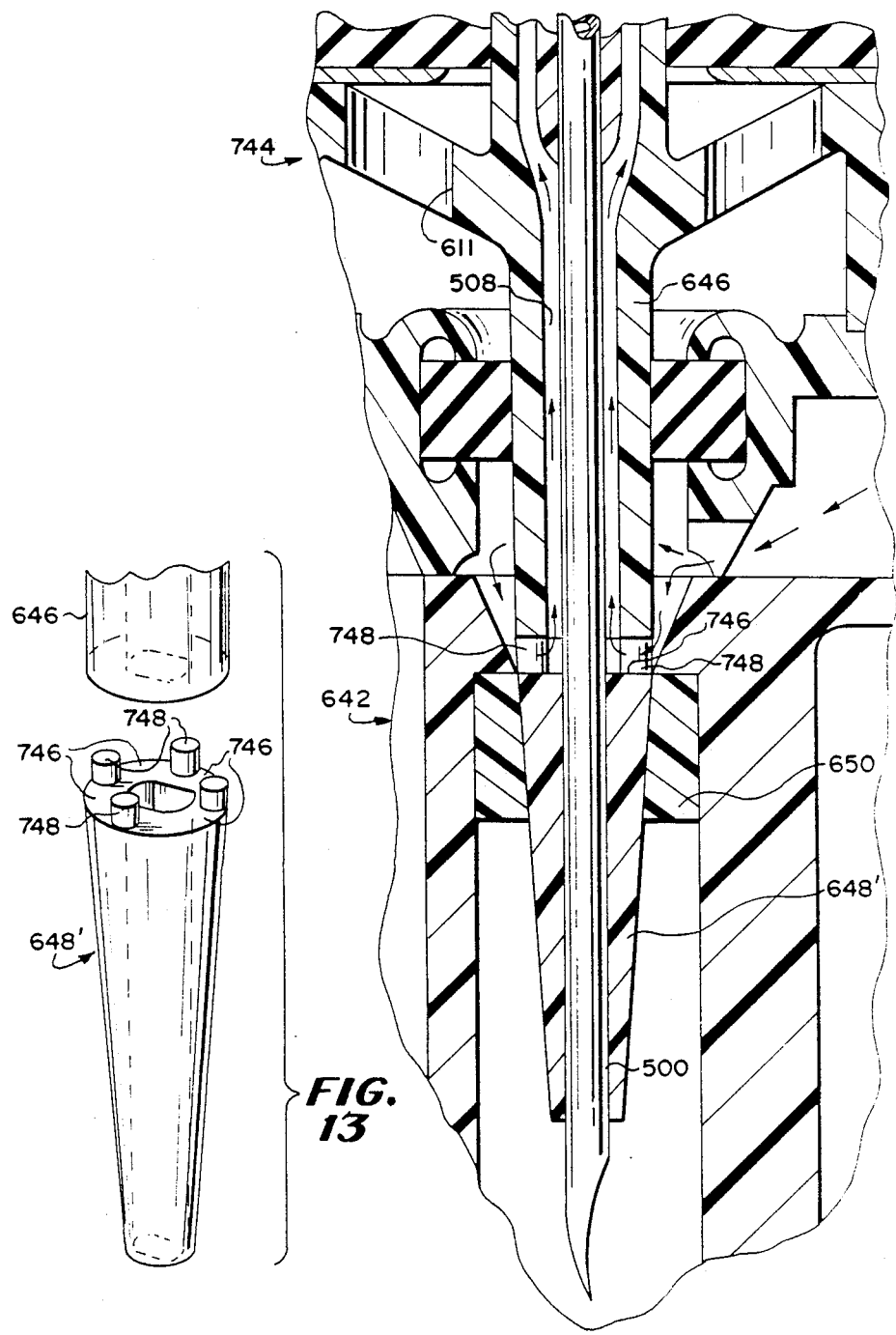

DRUG DELIVERY CARTRIDGE WITH PROTECTIVE COVER

The present application is filed concurrently with the application of Zdeb et al entitled "Cartridge and Adapter for Introducing a Beneficial Agent into an Intravenous Delivery System", U.S. patent application Ser. No. 114,817 now U.S. Pat. No. 4,804,366.

TECHNICAL FIELD OF THE INVENTION

The present invention is related to the delivery of a beneficial agent to a patient and is more particularly directed to a delivery system for introducing a beneficial agent into a fluid conduit.

BACKGROUND OF THE INVENTION

Many drugs are mixed with a diluent before being delivered intravenously to a patient. The diluent may be, for example, a dextrose solution, a saline solution or even water. Many such drugs are supplied in powder form and packaged in glass vials or ampules. Other drugs, such as some used in chemotherapy, are packaged in glass vials or ampules in a liquid state.

Powdered drugs may be reconstituted in a well known manner, utilizing a syringe which is used to inject liquid into the vial for mixing, the syringe eventually withdrawing the mixed solution from the vial. When a drug must be diluted before delivery to a patient the drug is often injected into a container of diluent after it is reconstituted, where the container may be connected to an administration set for delivery to a patient. More specifically, the diluent is often packaged in glass bottles, or flexible plastic containers such as are sold under the names MINI-BAG TM AND VIA-FLEX ® by Baxter Healthcare Corporation of Deerfield, Ill. These containers have administration ports for connection to an administration set which delivers the container contents from the container to the patient. The drug is typically added to the container through an injection site on the container.

Drugs may be packaged separately from the diluent for various reasons. One of the most important reasons is that many drugs do not retain their chemical and physical stability when mixed with a diluent and thus cannot be stored for any substantial period of time. Also, drugs are often packaged separately from the diluent because many firms which manufacture drugs are not engaged in the business of providing medical fluids in containers for intravenous delivery, and vice versa.

Therefore, a doctor, nurse, pharmacist or other medical personnel must mix the drug and diluent. This presents a number of problems. The reconstitution procedure is time consuming and requires aseptic technique. The operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming. Because of the limited vial volume, the increasing drug concentration in the diluent makes it harder to finish the reconstitution process. The operator may attempt to solve this by repeatedly injecting solution into the vial, mixing and withdrawing the solution but this makes necessary additional injections and movement of the syringe which increase the likelihood of contamination. Also, it is sometimes difficult to get all of the drug and/or liquid out of the vial, thus increasing the time required to perform the reconstitution procedure.

The reconstitution procedure should be performed under preferably sterile conditions. In addition to such a requirement making the operator justifiably more cautious and consuming more time, sterile conditions are often hard to maintain. In some instances, a laminar flow hood may be required under which the reconstitution procedure is performed.

Some drugs, such as some chemotherapy drugs, are toxic. Exposure of the operator to the drugs during reconstitution may be dangerous, especially if the operator works with such drugs on a daily basis and is repeatedly exposed to them.

A further problem is that the reconstitution procedure provides a source of confusion as to which container contains which drug. The diluent container should be marked with the drug with which it has been injected and the name of the patient to whom it should be delivered.

After a drug is reconstituted and withdrawn into a syringe barrel, the drug may in some instances be injected immediately into the intravenous system of a patient. More typically however, the reconstituted drug is injected from the syringe into a larger container of solution as discussed above, for connection to an intravenous administration set. This is because often the drug reconstituted in the syringe is still at a concentration so high as to cause local toxicity in the veins of a patient near the injection site where the needle pierces the skin. This may create severe vein irritation which may be medically harmful. Additionally, even though the proper dose of medication is in the syringe, immediate injection into the patient's blood stream may create a condition of systemic toxicity wherein the level of drug concentration in the patient's entire blood stream is dangerously high. Yet another reason for not making the injection from the syringe directly into the patient is that it creates an additional injection site into the patient, which may be painful for the patient and provides another opportunity for infection.

For these reasons, the reconstituted drug is more typically injected into a diluent container.

A patient may typically be administered a dextrose or saline solution from a large volume parenteral container, for example, such as a one liter container, delivered through an administration set such as a CONTINU-FLO ® administration set sold by Baxter Healthcare Corporation. If the reconstituted drug were injected into the large volume parenteral container, delivery of the drug would usually be made over too long a time period. Often, these large volume fluids are delivered at very slow flow rates.

More typically, the reconstituted drug is injected into a small volume parenteral container, such as a fifty milliliter container sold by Baxter Healthcare Corporation. This MINIBAG TM container is hung at a higher elevation than the large volume parenteral container and is connected by a secondary administration set to an injection site on the primary administration set. Because it is maintained at a higher elevation, the reconstituted drug in the small volume container is delivered, after which fluid from the large volume container begins to flow once more. By utilizing a small volume container connected to an administration set for delivery of the drug or other beneficial agent instead of a direct syringe injection, the drug is delivered over a preferred time period that tends to minimize negative side effects.

A closed reconstitution delivery system is disclosed in U.S. Pat. Nos. 4,410,321; 4,411,662; 4,432,755; and 4,458,733, all assigned to Baxter Travenol Laboratories Inc., the assignee of the present invention. As shown therein, a container includes a drug and a diluent in separate compartments which are reconstituted in a closed system before the drug is delivered to the patient. Typically, the container is connected to an administration set which is connected at its other end to the primary administration set, such as with the small volume parenteral container described above. The container shown in these patents solves many of the problems associated with syringe reconstitution. The product does however necessitate a series of reconstitution steps which must be performed by the nurse or other operator prior to delivering the fluid from the container.

Delivery of a drug or other beneficial agent in a manner not requiring reconstitution steps by an operator is shown in U.S. Pat. Nos. 4,424,056; 4,432,756; 4,439,183; 4,474,574; 4,479,793; 4,479,794; 4,525,162, and 4,548,599 and Canadian Pat. No. 1,173,795, assigned to Alza Corporation of Palo Alto, Cal. As disclosed in those patents, a parenteral delivery system is disclosed which has a formulation chamber therein for administering a beneficial agent such as a drug. The system is advantageous in that it provides for reconstitution of the drug by fluid flowing from a large volume parenteral container for example, through the administration set containing the formulation chamber with the drug therein. The system intends to eliminate the need for the time consuming reconstitution procedure described above and appears to eliminate the problems associated with the reconstitution procedure.

Another passive reconstitution system is disclosed in European Patent Application No. 0059694 to Aktiebolaget Hassle of Sweden.

Still another device for delivering a drug "in-line", i.e., in the administration set, is disclosed in U.S. Pat. No. 4,534,757 assigned to Alza Corporation. The device holds the drug and includes a section through which the liquid passes in a direction substantially opposite to the general direction in which liquid flows to the patient.

Yet another system which attempts to provide for drug reconstitution in-line without manual reconstitution by a nurse or other operator is shown in U.S. Pat. No. 4,465,471, assigned to Eli Lilly and Co. of Indianapolis, Ind. That patent discloses constructions for a receptacle in the administration set itself. A separate cartridge containing the drug to be reconstituted and delivered to the patient is plugged into the receptacle.

European Patent Application Publication No. 0146310 to Eli Lilly and Co., corresponding to U.S. Pat. No. 4,573,967, is directed to a system for drug reconstitution including an intravenous administration set and a drug vial and utilizes the vial vacuum to reconstitute the drug.

U.S. Pat. No. 4,534,758 to Akers et al. discloses a relatively complex drug delivery apparatus with various valves. When liquid from a container is delivered to the drug vial, the vial is to be agitated for a time sufficient to suspend the previously dry medicine.

U.S. Pat. No. 4,581,014 to Millerd et al. assigned to Ivac Corporation of San Diego, Calif. discloses a selector valve for delivering a previously reconstituted drug from a drug vial through an intravenous administration set to a patient.

All the publications described above are directed to solutions to the time consuming reconstitution procedure and/or its associated problems, such as delivery of the solution to a patient. In most of the offered solutions, delivery of the drug is intended to be passive, i.e., once the drug is placed into the administration set, manual reconstitution steps are not required.

Israel U.S. Pat. No. 4,589,867 discloses a delivery apparatus including an integral diluent container and a mixing container with an upward flow path.

Riddell U.S. Pat. No. 4,623,334 discloses delivery of a drug from an add-on vial in an upward flow path when made part of a fluid conduit to a patient. Israel and Riddell are principally directed to delivering liquid having a decreasing drug concentration over time, to a patient.

Ogle U.S. Pat. No. 3,941,171 is directed to a fluid transfer device including an adapter for connecting a chamber having a pierceable closure with another container. Air may exit the chamber at an elevation higher than the point at which liquid enters the chamber.

Still another common feature of many of the attempted solutions disclosed in these publications is that delivery of the drug is intended to be able to be made in a manner which is essentially independent of the fluid flow rate through the administration set and into the patient. Stated differently, some of the systems are designed to deliver a certain dosage of drug in a preselected time period, within a broad range of fluid flow rates. Delivery of a drug independent of flow rate is desirable because it ensures that the necessary dosage will be delivered within a therapeutically acceptable time period, which may be typically about twenty to thirty minutes, although this time period may vary depending upon the drug and dosage.

By making delivery of the drug or other beneficial agent independent of the flow rate, the system ensures that the drug will not be delivered too quickly should the flow rate be set too high by the nurse or other operator, thereby preventing the problem of systemic toxicity discussed above.

Some of the documents, such as U.S. Pat. Nos. 4,424,056; 4,479,793; and 4,479,794, are also directed to systems having a beneficial agent placed "in-line" in an administration set for mixing of the agent and delivery to a patient, wherein the delivery of the agent may be made in a given volume of fluid. Also, a valve controlling fluid flow may be manually operated to deliver the agent in a manner which can be made dependent upon fluid flow.

At least the automatic reconstitution type systems discussed above, (i.e., those not requiring a separate agitation or mixing step), suffer from the possibility of creating a concentration of beneficial agent in the fluid being delivered to the patient which is too high at low flow rates. This results in local toxicity to the patient near the point of introduction into the body. The problem is solved by the invention disclosed in U.S. patent application Ser. No. 721,999, filed Dec. 3, 1984, entitled "Drug Delivery Apparatus Preventing Local and Systemic Toxicity", Thomas E. Needham et al., assigned to the assignee of the present invention. Further solutions to the problems of passively mixing and delivering a beneficial agent to a patient are disclosed in U.S. patent application Ser. No. 721,991 filed Dec. 3, 1984 entitled "Housing Enabling Passive Mixing of a Beneficial Agent with a Diluent", Brain Zdeb et al., also assigned to the assignee of the present invention. In that application there is disclosed certain housing constructions for delivering the beneficial agent to the patient. Typically, the housing includes a receptacle which is placed in-line in a medical liquid administration set and a separate cartridge including the beneficial agent. The cartridge is plugged into the receptacle when it is desired to deliver the beneficial agent to the patient. Active reconstitution by a nurse or other operator is not required. Instead, once the cartridge is plugged into the receptacle, liquid flowing from the source of medical liquid through the administration set flows into the receptacle and the agent-containing cartridge, reconstituting the agent. The solution with agent therein flows out the receptacle, down the administration set to the patient's venous system.

Patent application Ser. No. 868,827 filed May 29, 1986 to Zdeb et al discloses a passive drug delivery system including a cartridge for introducing a beneficial agent into the fluid conduit of an administration set. An adapter means is mounted about the cartridge chamber holding the agent, for mounting the cartridge upon a receptacle in the fluid conduit and further providing for selective fluid communication between the receptacle and the chamber. The adapter means includes flow path means including chamber piercing means and receptacle piercing means. The application discloses two separate cannulas acting as the flow path means, which is important for creating the proper fluid path through the chamber to ensure proper mixing of the beneficial agent within the chamber. Liquid enters the chamber from the fluid conduit and moves downstream, back into the fluid conduit, to the patient.

In order to reduce cost to manufacture, simplify operation, and facilitate an easier and better connection between the cartridge and the receptacle, it would be desirable to eliminate one of the cannulas forming the flow path means between the beneficial agent and the fluid conduit. It would be desirable to accomplish these goals while retaining the beneficial flow path such as described in patent application U.S. Ser. No. 868,827. It would be desirable to meet these goals in a cartridge structure and also in an adapter structure for connecting the cartridge and the receptacle.

Furthermore, in order to prevent accidental, unintended activation of the cartridge and to avoid being stuck by the needle upon removal of the cartridge from the receptacle and to avoid exposure to small amounts of the beneficial agent, it would be desirable to have structure that would prevent unintentional unit activation and that would prevent exposure of the needle or other cannula to the nurse and other hospital personnel after administration of the beneficial agent and removal of the cartridge from the fluid conduit and receptacle.

It would also be desirable to have a unique receptacle that would permit the use of a single cannula in the flow path means between the receptacle and the cartridge, in a manner permitting the diversion of all fluid flow from the conduit into the cartridge when the cartridge is plugged into the receptacle and further permitting the free flow of fluid through the receptacle within the fluid conduit when the cartridge is not in place.

SUMMARY OF THE INVENTION

The present invention provides an improved drug delivery system including a cartridge for introducing a beneficial agent into a fluid conduit for delivery of the agent to a patient and including structure which both prevents inadvertent activation of the cartridge before intended use and which protects hospital personnel from an exposed needle or other cannula subsequent to use. The cartridge of the invention includes a rigid hollow tube and an agent-containing chamber slidably mounted at least partially within the hollow tube. In the first, pre-use position the chamber extends farther from the hollow tube than it does in a second position. At least one cannula is mounted to the hollow tube extending opposite the chamber. A protective cover or cap is originally in a chamber protective position wherein the cap is securely but releasably mounted to the hollow tube first end in order to cover the chamber and prevent movement of the chamber from the first to the second position. In the chamber protective position the cover prevents engagement of the chamber with flow path means, such as the cannula that pierces closure means to the chamber when the chamber is in the second position.

After the agent has been delivered to the patient, the cartridge is removed from the fluid conduit. The protective cover is then securely mounted about the second, opposite end of the hollow tube, covering the cannula, thereby protecting the nurse from the exposed cannula and any of the agent that might drip out of the cannula.

DESCRIPTION OF THE DRAWINGS

FIG. 1 is a perspective view of an adminstration set connected to an intravenous solution container and a patient, and including a receptacle for receiving the cartridge and adapter;

FIG. 2 is a perspective view of the cartridge including the adapter, flow path means, and protective cover;

FIG. 3 is a longitudinal cross-sectional view of the cartridge of FIG. 2;

FIG. 4 is an enlarged fragmentary cross-sectional view of the adapter and flow path means of the cartridge shown in FIG. 3;

FIG. 4A, when taken with FIG. 4, is a cross-sectional view of an adapter for a beneficial agent cartridge;

FIG. 5 is a cross-sectional view taken at line 5—5 of FIG. 4;

FIG. 6 is a perspective view of the cartridge of FIG. 2, after the chamber is engaged with the adapter means to activate the cartridge;

FIG. 7 is an enlarged fragmentary cross-sectional view of the receptacle shown in FIG. 1;

FIG. 9 is a perspective view of the cartridge of FIG. 2, with the protective cover adapted for engagement about the cannula and cartridge;

FIG. 10 is a perspective view as in FIG. 9, with the protective cover having been mounted about the cartridge;

FIG. 11 is a fragmentary, cross-sectional view of an alternate embodiment of the cartridge disposed upon a modified receptacle;

FIG. 12 is a fragmentary cross-sectional view of a still further embodiment of the cartridge, disposed upon a receptacle; and FIG. 13 is a fragmentary, exploded, perspective view of the shell shown in FIG. 12.

DETAILED DESCRIPTION OF THE PREFERRED EMBODIMENTS

Figure 8:
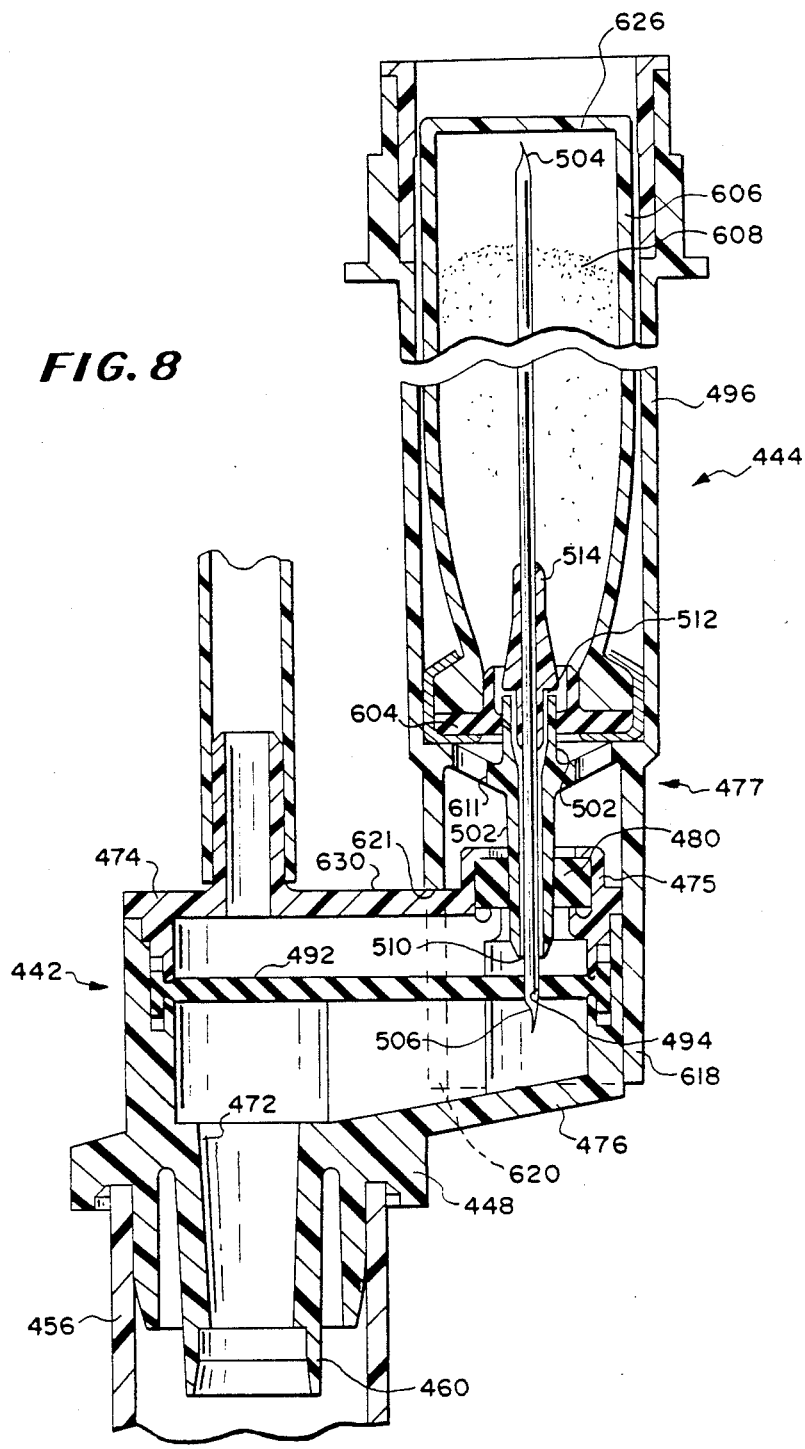
FIG. 8 is a longitudinal, cross-sectional view of the cartridge of FIG. 6 mounted upon the receptacle of FIG. 7.

Referring to FIG. 1, there is illustrated an administration set 420 for the delivery to a patient 426 of a medical liquid, stored within a medical liquid source such as large volume parenteral container 424. The administration set 420 includes a fluid conduit 428 made for example of flexible polyvinylchloride tubing. Upstream connection means such as a standard intravenous administration set spike 430 is mounted at the upstream end of the fluid conduit 428. The spike is adapted for piercing the membrane of the container administration port 432.

The fluid conduit 428 includes downstream connection means such as a Luer taper 434 mounted at the downstream end of the fluid conduit 428. The Luer taper 434 may be connected in accordance with standard technique to a venous catheter 436.

The administration set 420 may further include a standard pierceable injection situs 438 for injecting a medical liquid by means of a needle through the injection situs 438. The administration set 420 may further include flow rate control means such as a standard roller clamp 440 mounted about the flow conduit 428.

The administration set 420 further includes a unique receptacle 442 shown in greater detail in FIGS. 7 and 8. The receptacle 442 is an improvement to the receptacle disclosed in co-pending U.S. patent application Ser. Nos. 721,991, filed Dec. 3, 1984 now abandoned and 868,827, filed May 29, 1986, now abandoned both assigned to the assignee of the present invention. The receptacle 442 is mounted along the fluid conduit and is adapted for receiving a separate cartridge 444 containing beneficial agent, illustrated in FIGS. 2 through 6 and 8 through 10. When the cartridge is mounted upon the receptacle, virtually all liquid from the medical liquid source container 424 that flows through the fluid conduit 428 into the receptacle 442 also flows through the cartridge 444 before passing downstream out of the receptacle to the patient.

Downstream of the receptacle 442 is an air chamber 446, illustrated in FIG. 1. As will be explained in greater detail below, the air flask 446 permits automatic priming of the cartridge 444 upon mounting of the cartridge on the receptacle 442 of the administration set 420. The air flask 446 absorbs the air disposed within the cartridge 444 and prevents that air from passing downstream to the patient.

In the preferred embodiment, the receptacle 442 and air flask 446 are manufactured as a unit. The air flask 446 includes an inlet 448 integral with the receptacle 442. The inlet portion 448 defines a drop former 460, as illustrated in FIGS. 3 and 7. The receptacle receives fluid from upstream fluid conduit 428a. Liquid passing through both the receptacle 442 and air flask 446 exits the air flask outlet 450 and transfers to connected downstream fluid conduit 428b.

In the preferred embodiment, the air flask 446 includes an outlet cap 454. A cylindrical side wall 456 of preferably optically transparent, flexible material such as polyvinylchloride, is mounted between the flask inlet portion 448 and the outlet cap 454. The side wall 456, the flask inlet portion 448 and the outlet cap 454 together define an air chamber 458 having a cross-sectional diameter that is greater than the internal diameter of the fluid conduit 428. Thus, liquid entering the air chamber 458 from the drop-forming orifice 460 adjacent the inlet 448 falls toward the outlet 450. The air flask 446 provides a collection reservoir for air within the administration set 420.

The air flask 446 further includes particulate matter barrier means such as a particulate matter screen 462 mounted near the outlet 450. The particulate matter barrier may in fact be a sterilizing filter having a nominal pore size of about 0.2 micron. The nominal pore size may be much larger, such as a gross particulate matter barrier having a nominal pore size of about 20 microns. In the preferred embodiment the nominal pore size is about 10 microns. The screen may be a polyester or nylon mesh material such as supplied by Tetko of Switzerland. The particulate matter barrier 462 is mounted transverse to the fluid path such that all liquid passing through the air flask 446 must pass through the particulate matter barrier 462 before being delivered to the patient.

The particulate matter barrier 462 need not be disposed within the air flask 446 but the barrier should be mounted downstream of the receptacle 442 so that all liquid that exits the inserted cartridge 444 will pass through the particulate matter barrier.

In the preferred embodiment, the air flask 446 includes a minimum liquid level indicator 446 and a maximum liquid level indicator 468 which may for example comprise lines around the periphery of the air flask 446. The liquid level in the air flask 446 should preferably be somewhere between the minimum and maximum liquid level indicators 446, 468 immediately before insertion of the cartridge 444 within the receptacle 442.

As illustrated in FIGS. 7 and 8, the improved receptacle 442 includes a receptacle inlet 470 connected to the fluid conduit 428 and an outlet formed by the flask inlet portion 448. The air flask 446 is disposed downstream of the receptacle outlet 472. The receptacle inlet 470 and the air flask outlet 450 may be mounted to the fluid conduit 428 by means of interference fit, solvent bonding etc.

The receptacle 442 includes upper and lower fitments 474, 476 respectively. The upper fitment 474 includes the inlet. The lower fitment 476 includes the outlet 472. A piercable, resilient injection site 480 is mounted within the upper fitment 474 of the receptacle 442, such as by ultrasonically swaging a mount 475 for the injection site 480. The upper and lower fitments 474, 476 may be bonded together by adhesive, ultrasonic sealing etc. It is important that the injection site be securely maintained within the receptacle because a plurality of cartridges 444, each having a cannula, may be mounted on and removed from the injection site during the useful life of the receptacle 442 and administration set 420.

The receptacle 442 includes a resilient divider 492 trapped between the upper and lower fitments 474, 476 of the receptacle 442. The resilient divider defines a narrow through bore 494 directly below the resilient piercable injection site 480. As will be seen below, only that portion of the divider 492 that defines the through bore 494 utilizes resiliency as a desirable quality; however, for ease of manufacture, it is simple to define the through bore 494 with the divider 492, the divider 492 defining the flow path through the receptacle 442.

Before the cartridge of the present invention is engaged with the receptacle 442, fluid flowing from the parenteral container 424 flows through the fluid conduit 428 and through the receptacle inlet 470, whereupon it flows into the receptacle above the divider plate 492, through the through-bore 494 and downstream to the receptacle outlet 472 and downstream through the air flask 446 to the patient.

Turning now to FIGS. 2 through 6 and 8 through 10 there is shown the cartridge 444 and an adapter 477 for introducing a drug or other beneficial agent into the fluid conduit 28 at the receptacle 42, for delivery of the agent to a patient.

The cartridge 444 may include the adapter 477. Alternately, the adapter 477 may be a separate unit 477' suitable for connecting a beneficial agent chamber 606 with the receptacle 442.

Referring to FIGS. 2, 3, 4 and 5, and especially to FIG. 4, the cartridge 444 includes an adapter 477 having a rigid hollow cylinder or tube means 496 and a keyway wall 618, with the keyway wall 618 being part of the tube 496. A plate 498 is mounted across the tube 496 and defines the starting point for the keyway wall 618.

A rigid cannula 500 extends through the plate 498. A generally cylindrical shell 502 extends from both sides of the plate 498. The hollow tube 496, the plate 498 and the shell 502 may all be formed as a single piece of the same material such as a plastic.

The shell 502 is spaced from the cannula 500, with the shell 502 encompassing the cannula 500 but being shorter than either end of the cannula 500. The cannula 500 includes an inlet 504 and an outlet 506. In the preferred embodiment the inlet and outlet 504, 506 respectively are pointed to facilitate piercing. The cannula 500 is preferably but not necessarily made from a single piece.

The shell 502 is intermediate the cannula inlet and outlet 504, 506. The cannula 500 and the shell 502 define a channel 508 therebetween. In the preferred embodiment the periphery of the cannula 500 is circular along its length. Similarly, the internal surface 522 of the shell 502 is preferably arcuate and preferably circular along its length.

The channel 508 includes a channel inlet 510 defined between the shell 502 and the cannula 500, short of the cannula outlet 506. Similarly, the channel includes a channel outlet 512 defined by the shell 502 and the cannula 500, short of the cannula inlet 504.

A preferably plastic cannula holder 514 is secured to the cannula 500. The cannula holder 514 grips the cannula 500. As seen best in FIGS. 4 and 5, extension means 516 extend between the cannula holder 514 and the shell 502, across the channel 508, thereby securing the cannula 500 relative to the shell 502. In the preferred embodiment the extension means 516 is part of the holder 514.

The structure of the shell 502 surrounding the cannula 500 forms a channel of about 360°. Thus, the exterior portion 514a of the cannula holder 514 may be disposed fairly close to the channel outlet 504, the opening having a vertical height of only about 0.005 to 0.010 inch in the preferred embodiment. This is a much smaller dimension than presented when a separate cannula is used for the fluid flow into the cartridge chamber, such as shown in patent application Ser. No. 868,827, filed May 29, 1986. With this small size opening presented to the cartridge chamber, powdered beneficial agent within the chamber is prevented from exiting through the channel outlet 504 when the cartridge is activated.

As seen best in FIG. 4, in the preferred embodiment a portion of the cannula holder is disposed at least partially outside said shell 502 and includes a tapered portion or portions 518 to facilitate insertion through an injection site. Also, in the preferred embodiment this exterior portion 514a of the cannula holder 514 is mounted adjacent the channel outlet 512, short of the cannula inlet 504.

In the preferred embodiment at least a portion 514b of the holder 514 is disposed inside the shell 502. That portion 514b has a preferably substantially polyganol, preferably square cross-section which serves as the extension means 516. The corners 520 of the cannula holder portion 514b/extension means 516 fixedly engage the interior surface 522 of the shell, preferably by means of a secure friction fit.

Thus, with the described structure for the adapter 477, the cannula 500 is secured to the shell 502 while still maintaining an open flow path through the channel inlet 510, the channel 508 and the channel outlet 512. This is accomplished without complicated and expensive molds and molding techniques and without the use of any ultrasonic bond or adhesive or solvent to bond the cannula to the shell. Thus, a very small flow path is created outside a single cannula, with precision. It is desirable to exclude adhesives and/or solvents from contact with medical solutions and this is accomplished with the adapter of the present invention. Additionally, such substances, as well as ultrasonic welding, might tend to clog the small channel 508.

Referring to FIGS. 2 and 3, the cartridge 444 further includes a tubular chamber 606 containing a beneficial agent 608 such as a dry powdered drug, although the agent may also be a liquid. A pierceable stopper 604 or other closure means closes the tubular chamber 606.

Referring to FIGS. 3 and 4, the shell 502, along with the channel outlet 512 and the cannula inlet 504, are designed to pierce the pierceable stopper 604 or other injection site/closure means to the chamber 606 having the beneficial agent 608 therein. Similarly, the shell 502, along with the defined channel inlet 510, together with the cannula outlet 506, are designed to pierce the injection site 480 in the receptacle 442.

FIG. 4, as mentioned previously, is a fragmentary enlarged cross-sectional view of the adapter portion 477 of the cartridge 444 illustrated in FIG. 3. However, as stated above, the adapter 477 may be a separate unit adapter 477', illustrated by taking FIG. 4A in combination with FIG. 4. The first end 524 of the hollow tube 496 in adapter 477' may simply terminate such as in a plane perpendicular to the length of the tube 496 and preferably beyond the inlet end 504 of the cannula 500, as illustrated in FIG. 4A.

Referring once more to FIG. 3, the pierceable stopper 604 is mounted within the mouth 610 of the tubular chamber 606. The rubber stopper 604 may be secured within the tubular chamber 606 by means of a metal band 612 about the periphery of the mouth 610 and the rubber stopper 604, in the known manner for securing of a stopper in a standard drug vial. The chamber 606 may be a standard drug vial, depending on the required chamber dimensions, discussed below. The tubular chamber 606 is slidably mounted within the rigid cylinder 496 such that the rubber stopper 604 faces the plate 498. In place of the pierceable stopper, other pierceable closure means may be provided.

When the cartridge chamber 606 is in a first position illustrated in FIGS. 2 and 3, the rubber stopper 604 has not been pierced through by either the shell 502 or the cannula inlet 504. In the preferred embodiment, the pierceable stopper 604 remains spaced from the cannula 500 when the tubular cartridge 606 is in the first position.

The cannula 500 and the shell 502 comprise flow path means, which is part of the adapter means, which itself may be part of the cartridge 444. As seen in FIG. 2 and especially in FIG. 3, the hollow tube 496 is mounted about the chamber 606 and the adapter 477 facilitates mounting the cartridge 444 upon the receptacle 442. The adapter 477 slides relative to chamber 606. Stated differently, the tubular chamber 606 and the adapter 477 are selectively slidable relative to each other.

The adapter means preferably includes the keyway means extending on the side of the base plate opposite of the chamber 606 and substantially coaxial therewith, and forming part of the tube means 496. The keyway means may include a relatively rigid keyway wall 618 having a keyway slot 620 for fitting over the receptacle 442. The keyway means ensures proper engagement of the cartridge 444 with the associated receptacle 442, including the proper disposition of the cannula outlet 506, shell 502 and channel inlet 510 within the receptacle 442, as seen in FIG. 8.

Referring to FIGS. 2 and 3, the cartridge 444 also includes a cartridge-removable cannula cover 601 removably secured within the base plate 498. The cartridge-removable cannula cover 601 has as its principal purpose preventing the connection of the cartridge 444 to the receptacle 442 without first piercing the stopper 604 with the cannula 500 and shell 502. The cannula cover 601 ensures that the chamber 606 must be moved from the first position illustrated in FIGS. 2 and 3 to the second position illustrated in FIGS. 6 and 8 before the cartridge 444 can be mounted upon the receptacle 442. Should the cartridge be mounted prematurely, i.e., before the cartridge is moved to the second position, liquid flowing through the administration set would spill out of the shell 502 at the channel outlet 512 without entering the cartridge chamber 606.

Because of the relatively small dimensions of the keyway wall 618, the cannula cover 601 cannot be removed from the cartridge 444 when the cannula cover 601 is disposed as shown in FIGS. 2 and 3.

The cannula cover 601 includes pins 603, including a reduced pin portion 605 at the distal end of each pin and an enlarged pin, portion 542 at the proximal end of each pin. The pins extend from a circular cannula cover base 609. The cannula cover base 609 fits snugly but not tightly against the keyway wall 618. Openings 611 extend through the plate 498 and receive the enlarged pin portions 542 of the pins 603, preferably in interference fit so that the cannula cover 601 will not inadvertently become detached from the plate 498.

The chamber 606 of the cartridge 444 is slidable from the first position shown in FIGS. 2 and 3 to a second position illustrated in FIGS. 6 and 8 by pushing the chamber 606 down within the rigid cylinder 496 until the pierceable stopper 604 or the metal band 612 thereabout abuts the plate 498, which serves as a stop. In this second position, the cannula inlet 504, the cannula holder 514, the shell 502 and the defined channel outlet 512 have pierced the stopper 604 or other second resilient injection site. Thus, within the chamber interior, the channel outlet 512 and the cannula inlet 504 are in fluid communication. The cannula inlet 504 is well within the tubular chamber, preferably near the top end 626 of the chamber 606. This is best illustrated in FIG. 8, wherein it is also shown that the defined channel outlet 512 is preferably just within the tubular chamber 606. This second position is also illustrated in FIG. 6.

Because the shell that forms the channel outlet 512 and the base plate 498 acting as the stop are preferably molded from a single piece, it is easy to consistently manufacture a cartridge 444 with a fixed distance between the channel outlet 512 and the stopper 604. It is important to control this distance when planning for the mixing action within the chamber.

The cartridge 444 also includes a protective cap or cover 530 initially disposed in a chamber protective position covering the chamber 606, as seen for example in FIGS. 2 and 3. In the preferred embodiment the protective cover 530 includes a top 532 and a skirt 534 depending from the top 532. The free end portion 536 of the skirt 534 fits snugly about the first end 497 of the hollow tube 496. In the preferred embodiment, both the first end 497 of the tube 496 and the free end portion 536 of the protective cap 530 are enlarged so as to fit about the structural support 538 of the hollow tube 496, provided so as to securely retain the chamber 606 about the mouth 610 thereof.

In operation, before a beneficial agent 608 in the cartridge is delivered to the patient, the administration set 420 of the invention operates by providing an open fluid pathway between the medical liquid container 424 and the patient 426, as illustrated in FIG. 1. Liquid 422 flows from the container 424 through the administration port 432 and spike 430. The liquid flows through the fluid conduit 428 and through the receptacle 442, following the pathway through the receptacle inlet 470, through-bore 494 and outlet 472, in that order. Liquid flows into the air flask 446 through the drop former 460. Any air from upstream collects within the air flask 446 and liquid continues to flow downstream through the flask outlet 450 through the downstream conduit portion 428b and into the patient through the Luer connection 434 and venous catheter 436.

Before the administration set 420 is placed in communication with the patient 426, the fluid conduit 428 is primed, i.e., air is eliminated. This is performed in the known manner, by allowing liquid to flow through the set 420 before connection to the patient.

To raise the liquid level up to a level 628 within the flask 446 such that it is between the minimum and maximum indicator lines 466, 468, the air flask sidewall 456 may be squeezed and released such as with most drip chambers, in the standard manner.

When it is desired to deliver a beneficial agent 608 such as a drug to the patient, the cartridge 444 having the beneficial agent 608 therein is mounted upon the receptacle 442 as shown in FIG. 8.

The cartridge is provided to the nurse or other medical personnel as illustrated in FIGS. 2 and 3, with the chamber 606 in the first position. The protective cap 530 prevents any urging of the chamber 606 so as to prevent its engagement with the cannula 500 and the shell 502. The cover 530 may also assist in retaining the chamber 606 within the tube 496 when the chamber 606 is in the first position. A shrink wrap band 534 may be disposed about the free end portion 536 of the cap 530 and about the first end 497 of the hollow tube 496. Together with the snug friction fit of the free end portion 536, the shrink wrap prevents accidental removal of the protective cover 530.

Typically, the cartridge 444 will be packaged in another, sterile container to assure the sterility of the cartridge interior, including the cannula 500, the shell 502, and the pierceable stopper 604. However, it is possible that the protective cover 530, the hollow tube 496 and the removable needle cover 601 may maintain the exposed portion of the pierceable stopper 604 and the cannula 500 and shell 502 in aseptic condition.

To activate the cartridge, the shrink wrap band 534 is torn away. The nurse removes the protective cover 530 from the remainder of the cartridge. The operator then grasps the rigid tube 496 and pushes down on the top 626 of the chamber 606 with the thumb, thereby slidably moving the cartridge chamber 606 within the hollow tube 496. In this one action, first the cannula inlet 504 and then the shell 502 pierce the pierceable stopper 604. In the preferred construction illustrated in the drawings, after the cannula inlet 504 pierces the stopper, the cannula holder 514 pierces the stopper, followed by the shell 502, with the shell 502 and the cannula holder 514 defining the channel outlet 512, which is now disposed slightly within the chamber 606. In the same motion, the chamber 606 continues to be urged into the hollow tube 496 until it engages the pins 603 of the cannula cover 601, forcing the enlarged pin portions 542 out of the openings 611 in the plate 498. When the chamber 606 comes to the stop adjacent the plate 498, only the reduced pin portions 605 remain within the opening 611, so that the operator may easily grasp the cannula cover 601, now projecting past the end of the keyway wall 618. Alternatively, since the narrower pin portions 605 are now within the openings 611, there is no longer an interference fit between the plate 498 and the cannula cover 601, so that the cannula cover 601 will now preferably simply fall out of the cartridge 444.

It should be noted that in addition to preventing improper mounting of the cartridge 444 upon the receptacle 442 as explained above, the needle cover 601 also prevents touch contamination of the cannula 500 until activation of the cartridge 444.

With the cartridge chamber 606 now in the second position, the cartridge 444 is mounted upon the receptacle 442 as illustrated in FIG. 8 by grasping the receptacle 442 in one hand and the rigid cylinder 496 in the other hand and pushing the cartridge down so that the cannula outlet 506 and then the shell 502 with defined channel inlet 510 both pierce the first resilient injection site 480, which in the preferred embodiment is the injection site on the receptacle. The cartridge 444 continues to be urged downwardly so that the cannula outlet 506 enters the through-bore 494 and is liquid-sealingly engaged by the resilient divider 492 around the periphery of the cannula outlet portion 506. Unlike the cartridge disclosed in U.S. patent application Ser. No. 868,827 to Zdeb et al having two separate cannulas, the rotational positioning of the cartridge 444 relative to the receptacle 442 is not critical with the device of the present invention. However, the vertical positioning of the cannula outlet 506 and the shell 502 with defined channel inlet 510, relative to the receptacle, is important. This proper vertical positioning of the cartridge 444 relative to the receptacle 442 is assured by the keyway wall 618 and keyway slot 620. The keyway slot 620 is guided over the bridge 630 of the upper fitment 474 on the receptacle 442. Downward movement of the cartridge upon the receptacle is limited by the slot top 621 abutting the bridge 630 of the receptacle. Further downward movement of the cartridge is not possible and thus proper vertical positioning of the cannula outlet 506 and the channel inlet 510 within the receptacle is assured.

Proper installation has occurred when as noted the slot top 421 abuts the bridge 630. Alternatively, other stops could of course be implemented, such as the plate 498 abutting the injection site 480.

After the cartridge is thus mounted about the receptacle, the nurse or other operator may either place the protective cover 530 in a pocket or may remount the protective cover about the first end 497 of the hollow tube 496.

Upon engagement of the cartridge 444 and receptacle 442 as illustrated in FIG. 8, liquid 422 flowing into the receptacle at the inlet 470 is prevented from passing through the through-bore 494 and out the receptacle 442 because the resilient divider 492 has been sealed about the cannula outlet portion 506 at the through-bore 494. Thus, liquid entering the receptacle 442 enters the channel inlet 510, flows through the channel 508 and enters the tubular chamber 506 at the channel outlet 512.

As liquid rises within the chamber 606, residual air within the chamber is forced downstream through the cannula inlet 504 and then the cannula outlet 506. The air enters the air flask 446 through the drop former 460 and collects within the flask 446. The initial liquid level 628 illustrated in FIG. 1 drops to a new level. The liquid level 628 should be above the minimum liquid level indicator line before insertion of the cartridge 444 into the administration set 420 so that as air exits the cartridge 444, the liquid level within the air flask 446 will not drop to the flask outlet 450 where it could be trapped and forced downstream to the patient. The liquid level after cartridge priming may be below the minimum liquid level 466, but if it is above the minimum line 466 before insertion of the cartridge 444, the liquid level will never be as low as the outlet 450.

The maximum liquid level indicator 468 serves as a guide for the maximum liquid level so that liquid drops entering the air flask through the drop former 460 may still be counted in the manner of a standard drip chamber.

The liquid level within the tubular chamber 606 continues to rise until it reaches the cannula inlet 504, whereupon liquid begins to exit the chamber 606 through the cannula 500, downstream through the cannula outlet 506 and into the air flask 446 through the drop former 460. Liquid exiting the chamber 606 has an appropriate concentration of beneficial agent 608 mixed therewith for delivery to the patient. The upward liquid flow path created within the chamber 606 by the shell 502, channel 508 and cannula 500 creates a density gradient within the chamber 606 such that the concentration of drug within the liquid 422 exiting at cannula outlet 506 will not be so high as to create local toxicity to the patient. Local toxicity is a situation in which vein irritation can occur near the venous injection site when drug concentrations within the delivery liquid 422 are too high.

If a separate adapter 477', as illustrated in the combined FIG. 4, FIG. 4A is utilized instead of the adapter 477 which is part of the cartridge 444, a chamber 606 is inserted into the hollow tube 496 at the top end 524 thereof, thereby installing the chamber 606 within the adapter 477' as described with the cartridge 444 and adapter 477 above. The chamber 606 is urged toward the plate 498 until the cannula inlet 504 and then the coaxial shell with the channel outlet 512 pierce the stopper 604 and the chamber hits the plate 498 or other stop. The adapter 477', with the chamber 606 mounted therein, is mounted about the receptacle 442 in the same manner as described above relative to the cartridge 444 with adapter 477. The fluid flow path through the fluid conduit 428, the receptacle 442, the chamber 606 and adapter 477′ is the same as described above relative to the cartridge 444 and receptacle 442. The separate unit adapter 477′ may be packaged in a sterile wrap or package.

At typical liquid flow rates, the amount of drug delivered to the patient per unit time is generally independent of the flow rate. This means that at extremely high flow rates, the total amount of drug delivered to the patient per unit time will not be so high as to cause systemic toxicity to the patient. Stated differently, the patient will not have too much drug introduced into the body in too short a time period.

It is believed that at lower liquid flow rates the rate of drug delivered to the patient per unit time tends to become more dependent upon the liquid flow rate through the administration set 420. However, local toxicity to the patient will not occur. It is believed that the upper limit on the drug concentration within liquid 422 exiting the chamber 606 is limited to a safe maximum for two principle reasons. First, the density gradient created within the columnar tubular chamber 606 means that the concentration of liquid 422 at the point of entry into the cannula inlet 504 is the lowest of any elevation within the tubular chamber 606. Secondly, as the liquid flow rate through the administration set 420 decreases, which would ordinarily increase the risk of an unacceptably high drug concentration to the patient, the amount of mixing and liquid turbulance created within the chamber 606 also decreases, exaggerating the density gradient so that the difference in densities from the area of the stopper 604 to the cannula inlet 504 becomes greater.

It is to be noted that the different liquid flow rates mentioned above are only possibilities; in the preferred manner of operation, the nurse or other medical personnel would set an acceptable flow rate with the flow rate control means (such as the roller clamp 440 or a peristaltic pump) and not adjust the liquid flow rate again, at least until after delivery of the beneficial agent 608.

The administration set 420, with the unique cartridge 444 and receptacle 442, are capable of delivering a therapeutically beneficial amount of a beneficial agent 608 within a therapeutically acceptable time period. For example, a one gram dose of ampicillin in the chamber 606 may be delivered in about thirty minutes at a liquid flow rate of 120 mls per hour.

In the preferred embodiment, the tubular chamber 606 has a volume of about 10 mls, and may include up to about 3 to 4 mls of air. The internal diameter of the tubular chamber is about 0.4 inch. The height of the tubular chamber from the mouth 610 to the top 526 is about two inches. The relatively long, narrow configuration of the chamber 606 is also believed to assist in mixing the beneficial agent 608 with the liquid 422. The liquid 422 may be a 5% dextrose solution for example.

By varying the dimensions of the tubular chamber 606 the delivery profile for the beneficial agent 608 may be changed. For example, by enlarging the internal diameter of the tubular chamber, it will take longer to deliver the agent 608 within the chamber 606 to the patient 26. Similarly, lengthening the chamber 606 will also increase the delivery time if the cannula 500 is also extended within the longer chamber.

As noted previously, more than one cartridge 444 may be utilized during the use of a single administration set 420. If so, the cartridge 444 must be removed from the receptacle 442 and disposed of so that another cartridge 444 may be installed upon the receptacle 442.

As the cartridge 444 is pulled off the receptacle, the through-bore 494 is once more opened so that the fluid flow path will resume as described earlier, before insertion of the first cartridge. As the shell 502 and cannula 500 are withdrawn, the resilient injection site 480 will reseal. Now, to avoid dripping of any liquid out of the tubular chamber 606 and to prevent any possibility of personnel being stuck by the cannula outlet 506, the protective cover 530 is installed over the tube 496 and cannula outlet 506 such as illustrated in FIGS. 9 and 10. In this cannula protective position, the used cartridge 444 has no exposed cannula point. Any liquid dripping out of the chamber 606 will simply collect harmlessly within the protective cap 530, which engages the cartridge 444 by friction fit about the outside of the tube 496.

Referring now to FIG. 11, there is disclosed a cartridge 644 and a receptacle 642 according to another embodiment of the invention. In this embodiment the shell 646 is identical to the shell 502 on that side of the plate 499 that defines the channel outlet 512. However, the shell 646 extends further toward the cannula outlet 506 so that it is the shell portion 648 adjacent the cannula outlet 506, instead of the cannula outlet portion 506 itself, that is liquid-sealingly engaged about the exterior thereof when the cartridge 644 is mounted on the receptacle 642. Although a receptacle such as receptacle 442 with the resilient divider 492 could be utilized, here the receptacle 642 includes a resilient bushing 650 similar to the receptacle illustrated in U.S. patent application Ser. No. 868,827 to Zdeb et al. The receptacle 642 includes upper and lower fitments 652, 654 respectively. The resilient bushing 650 is mounted within the lower fitment 654, directly below the injection site 480 and includes a through-bore 656 larger than the through-bore 494 of the resilient divider 492 so as to permit the shell portion 648 to enter the through-bore 656 for liquid-sealing engagement between the bushing 650 and the shell portion 648.

In this embodiment, the defined channel inlet 658 is disposed within the sidewall 660 of the shell 646, 648, spaced sufficiently above the cannula outlet 506 so that it is above the bushing 650 and not encompassed by the bushing 650, thereby permitting fluid flow into the channel inlet 658 from the receptacle inlet 662.

The lower fitment 654 of the receptacle 642 may include a tapered introducer portion 664 to ensure proper introduction of the cannula outlet 506 and shell portion 648 within the resilient bushing 650.

Thus, with the cartridge 644 and receptacle 642 illustrated in FIG. 11, liquid flowing into the receptacle through the inlet 662 flows into the channel inlet 658, upwardly through the defined channel 508 and out the defined channel outlet 512 into the chamber 606 having a beneficial agent 608 therein. Liquid flows upwardly in the chamber to the cannula inlet 504, whereupon it flows down out the cannula outlet 506, through the drop former 460 and downstream to the patient.

Referring now to FIGS. 12 and 13, there is shown yet another embodiment of the invention. A cartridge 744 is similar to the cartridge 644 and may be employed with the receptacle 642 of FIG. 11. Here, the shell portion 648′, that engages the bushing 650 in the same manner as the bushing 648, is a separate part from the remainder of the shell 646 and includes at least one and preferably a plurality of channel inlets 746 defined by posts 748 that extend from the separate shell portion 648' and which abut the remainder of the shell 646.

FIG. 13 illustrates the shell 646 before installation with the cannula 500. The flow path of fluid through the receptacle and the cartridge 744 is the same as described relative to FIG. 11.

The embodiments of the cartridge illustrated in FIGS. 11–13 will also work with the receptacle illustrated in FIG. 7.

While several embodiments and features have been described in detail herein and shown in the accompanying drawings, it will be evident that various further modifications are possible without departing from the scope of the claimed invention.

What is claimed is:

1. A cartridge for introducing a beneficial agent into a fluid conduit for delivery of the beneficial agent, said cartridge comprising;
    (a) a rigid hollow tube;
    (b) a chamber having a beneficial agent therein, said chamber being mounted adjacent a first end of said hollow tube and being slidably mounted at least partially within said hollow tube from a first position to a second position, such that in said first position said chamber extends a greater distance from said hollow tube than in said second position;
    (c) at least one cannula mounted within said hollow tube, extending at least in a direction opposite said chamber; and
    (d) a protective cover selectively movable between a chamber protective position wherein said cover is securely but releasably mounted to said tube adjacent said first end thereof to cover said chamber and prevent movement of said chamber from said first position to said second position, and a cannula protective position wherein said protective cover is securely mounted about the other end of said hollow tube, covering said cannula.

2. The cartridge as in claim 1, further wherein said protective cover comprises a top, a skirt portion depending from said top and an enlarged open end portion for engaging said hollow tube.

3. The cartridge as in claim 1, wherein said protective cover is generally cup shaped.

* * * * *